US012521281B1

(12) United States Patent
Noguera

(10) Patent No.: US 12,521,281 B1
(45) Date of Patent: Jan. 13, 2026

(54) COMPRESSION LEGWEAR WITH LINEAR PADS TO CONTROL SYMPTOMS OF VARICOSE VEINS

(71) Applicant: Norman Noguera, Sherman Oaks, CA (US)

(72) Inventor: Norman Noguera, Sherman Oaks, CA (US)

(*) Notice: Subject to any disclaimer, the term of this patent is extended or adjusted under 35 U.S.C. 154(b) by 0 days.

(21) Appl. No.: 18/941,607

(22) Filed: Nov. 8, 2024

(51) Int. Cl.

| | |
|---|---|
| ***A61F 13/00*** | (2024.01) |
| ***A41B 11/02*** | (2006.01) |
| ***A61F 13/06*** | (2006.01) |

(52) U.S. Cl.
CPC .............. *A61F 13/06* (2013.01); *A41B 11/02* (2013.01)

(58) Field of Classification Search
CPC .............. A61F 13/01008; A61F 13/022; A61F 13/068; A61F 13/12; A61F 13/471; A61F 15/008; A61F 2/02; A61F 2/583; A61F 2/586; A61F 2/66; A61F 2/6607; A61F 2/74; A61F 2/9517; A61F 2002/30235; A61F 2002/30405; A61F 2002/30772; A61F 2002/501; A61F 2002/5027; A61F 2002/5038; A61F 2002/5039; A61F 2002/505; A61F 2002/7615; A61F 2002/762; A61F 2002/7675; A61F 2005/0155; A61F 2005/414; A61F 2007/0021; A61F 2007/0037; A61F 2007/0226; A61F 2007/0242; A61F 2007/0285; A61F 2013/00157; A61F 2013/00285; A61F 2013/8408; A61F 2013/8414; A61F 2250/0018; A61F 5/0003; A61F 5/004; A61F 5/0043; A61F 5/0076; A61F 5/10; A61F 5/24; A61F 5/41; A61F 5/48; A61F 13/01034; A61F 13/0259; A61F 13/2085; A61F 13/505; A61F 13/51104; A61F 13/531; A61F 13/538; A61F 15/00; A61F 2/0004; A61F 2/0031; A61F 2/12; A61F 2/38; A61F 2/482; A61F 2/52; A61F 2/68; A61F 2/7843; A61F 2/848; A61F 2/966; A61F 2002/5024; A61F 2002/5072; A61F 2002/5081; A61F 2002/5083; A61F 2002/543; A61F 2002/546; A61F 2002/608; A61F 2002/6657; A61F 2002/704;

(Continued)

(56) References Cited

U.S. PATENT DOCUMENTS

| | | | |
|---|---|---|---|
| 3,515,773 | A | 6/1970 | Dahl |
| 3,756,848 | A | 9/1973 | Dahl |

(Continued)

FOREIGN PATENT DOCUMENTS

| | | |
|---|---|---|
| CN | 2015070771 | 5/2015 |
| DE | 20080404 | 4/2008 |

(Continued)

OTHER PUBLICATIONS

WO 2006134875 translation (Year: 2006).*

*Primary Examiner* — Kim M Lewis
(74) *Attorney, Agent, or Firm* — Jerome Drabiak; Edison Law Group

(57) ABSTRACT

Knee-high and thigh-high compression legwear for right and left legs are disclosed. The legwear, made to be worn by people who have varicose veins, includes elongated pads that are adapted and configured to exert a pressure of about 20-30 mm Hg over the veins.

10 Claims, 9 Drawing Sheets

(58) Field of Classification Search

CPC ........ A61F 2002/7831; A61F 2002/785; A61F 2005/0169; A61F 2005/0197; A61F 2007/0002; A61F 2007/004; A61F 2007/0069; A61F 2007/0076; A61F 2007/0215; A61F 2007/0217; A61F 2007/0246; A61F 2007/0292; A61F 2013/00097; A61F 2013/00136; A61F 2013/00229; A61F 2013/00272; A61F 2013/00519; A61F 2013/00617; A61F 2013/00731; A61F 2013/00748; A61F 2013/00855; A61F 2013/00919; A61F 2013/00944; A61F 2013/424; A61F 2013/4518; A61F 2013/51026; A61F 2013/51061; A61F 2013/51066; A61F 2013/530007; A61F 2013/530233; A61F 2013/530802; A61F 2013/8473; A61F 2210/0057; A61F 2230/0006; A61F 2250/0002; A61F 2250/0004; A61F 5/04; A61F 5/055; A61F 5/05866; A61F 5/4553; A61F 13/00085; A61F 13/0203; A61F 13/067; A61F 13/2088; A61F 15/001; A61F 2/0009; A61F 2/1678; A61F 2/4455; A61F 2/484; A61F 2/5044; A61F 2/64; A61F 2002/2835; A61F 2002/3008; A61F 2002/30112; A61F 2002/30507; A61F 2002/30563; A61F 2002/30622; A61F 2002/5001; A61F 2002/5003; A61F 2002/5018; A61F 2002/5033; A61F 2002/5052; A61F 2002/665; A61F 2002/6664; A61F 2002/6827; A61F 2002/705; A61F 2005/0132; A61F 2005/0141; A61F 2005/0144; A61F 2005/0183; A61F 2007/0057; A61F 2007/0058; A61F 2007/0279; A61F 2013/00131; A61F 2013/00553; A61F 2013/00634; A61F 2013/0094; A61F 2013/15024; A61F 2220/0033; A61F 2230/0004; A61F 2250/0012; A61F 2310/00173; A61F 5/058; A61F 5/3715; A61F 5/3753; A61F 13/023; A61F 13/065; A61F 13/102; A61F 13/105; A61F 13/15; A61F 13/511; A61F 13/514; A61F 13/5616; A61F 13/64; A61F 15/02; A61F 2/0039; A61F 2/005; A61F 2/0077; A61F 2/167; A61F 2/2409; A61F 2/2418; A61F 2/2427; A61F 2/2433; A61F 2/2457; A61F 2/2803; A61F 2/30965; A61F 2/54; A61F 2/601; A61F 2/70; A61F 2/741; A61F 2/748; A61F 2002/30074; A61F 2002/30092; A61F 2002/30113; A61F 2002/3013; A61F 2002/30153; A61F 2002/30158; A61F 2002/30215; A61F 2002/30233; A61F 2002/30276; A61F 2002/30327; A61F 2002/30461; A61F 2002/30492; A61F 2002/30494; A61F 2002/30706; A61F 2002/3071; A61F 2002/5006; A61F 2002/5012; A61F 2002/502; A61F 2002/5041; A61F 2002/5043; A61F 2002/5066; A61F 2002/5075; A61F 2002/5087; A61F 2002/6628; A61F 2002/701; A61F 2002/707; A61F 2002/7887; A61F 2002/805; A61F 2005/002; A61F 2005/0023; A61F 2007/0003; A61F 2007/0022; A61F 2007/0023; A61F 2007/0047; A61F 2007/0065; A61F 2007/0072; A61F 2007/0073; A61F 2007/0222; A61F 2007/0247; A61F 2007/0258; A61F 2007/026; A61F 2007/101; A61F 2013/00089; A61F 2013/00578; A61F 2013/00604; A61F 2013/00651; A61F 2013/00702; A61F 2013/15284; A61F 2013/15292; A61F 2013/015357; A61F 2013/1543; A61F 2013/4568; A61F 2013/51023; A61F 2013/51028; A61F 2013/51092; A61F 2013/51147; A61F 2013/51411; A61F 2013/51413; A61F 2013/51415; A61F 2210/009; A61F 2220/0016; A61F 2230/0026; A61F 2230/0086; A61F 2250/0059; A61F 2250/0069; A61F 2250/0082; A61F 2250/0089; A61F 2250/0096; A61F 2310/00377; A61F 5/0026; A61F 5/0069; A61F 5/042; A61F 5/048; A61F 5/05825; A61F 5/05833; A61F 5/4408; A61F 6/08; A61F 9/00; A61F 9/04; A61F 13/0236; A61F 13/025; A61F 13/0253; A61F 13/0269; A61F 13/0276; A61F 13/063; A61F 13/128; A61F 13/148; A61F 13/20; A61F 13/2054; A61F 13/551; A61F 13/5511; A61F 13/55115; A61F 13/60; A61F 13/82; A61F 15/005; A61F 15/006; A61F 2/022; A61F 2/042; A61F 2/1691; A61F 2/20; A61F 2/24; A61F 2/2415; A61F 2/246; A61F 2/2463; A61F 2/2466; A61F 2/2476; A61F 2/30721; A61F 2/30734; A61F 2/30767; A61F 2/30907; A61F 2/3603; A61F 2/4225; A61F 2/44; A61F 2/48; A61F 2/50; A61F 2/582; A61F 2/588; A61F 2/644; A61F 2/742; A61F 2/962; A61F 2002/047; A61F 2002/0894; A61F 2002/2821; A61F 2002/30011; A61F 2002/30014; A61F 2002/30131; A61F 2002/30133; A61F 2002/30159; A61F 2002/30217; A61F 2002/30242; A61F 2002/30245; A61F 2002/30332; A61F 2002/30345; A61F 2002/30428; A61F 2002/30467; A61F 2002/30522; A61F 2002/30571; A61F 2002/30589; A61F 2002/30593; A61F 2002/30594; A61F 2002/30604; A61F 2002/30624; A61F 2002/30649; A61F 2002/30652; A61F 2002/30738; A61F 2002/30822; A61F 2002/30836; A61F 2002/30968; A61F 2002/3097; A61F 2002/3605; A61F 2002/3631; A61F 2002/365; A61F 2002/4677; A61F 2002/5015; A61F 2002/5026; A61F 2002/5032; A61F 2002/5047; A61F 2002/5049; A61F 2002/5064; A61F 2002/5089; A61F 2002/607; A61F 2002/6678; A61F 2002/6818; A61F 2002/689; A61F 2002/7605; A61F 2002/763; A61F 2002/7875; A61F 2002/7881; A61F 2002/807; A61F 2002/9528; A61F 2002/9665; A61F 2005/415; A61F 2005/4402; A61F 2006/049; A61F

2007/0004; A61F 2007/0007; A61F 2007/0011; A61F 2007/0013; A61F 2007/0014; A61F 2007/0015; A61F 2007/0017; A61F 2007/0024; A61F 2007/0038; A61F 2007/0046; A61F 2007/005; A61F 2007/0051; A61F 2007/0052; A61F 2007/008; A61F 2007/0204; A61F 2007/0209; A61F 2007/0214; A61F 2007/0223; A61F 2007/0239; A61F 2007/0249; A61F 2007/0261; A61F 2007/0269; A61F 2007/0287; A61F 2007/029; A61F 2007/126; A61F 2013/00106; A61F 2013/00127; A61F 2013/00165; A61F 2013/00182; A61F 2013/00191; A61F 2013/00242; A61F 2013/00251; A61F 2013/00276; A61F 2013/00293; A61F 2013/00327; A61F 2013/00382; A61F 2013/00387; A61F 2013/00395; A61F 2013/00404; A61F 2013/00408; A61F 2013/0048; A61F 2013/00489; A61F 2013/0057; A61F 2013/00655; A61F 2013/00778; A61F 2013/00846; A61F 2013/00889; A61F 2013/15008; A61F 2013/15081; A61F 2013/423; A61F 2220/0066; A61F 2220/0083; A61F 2220/0091; A61F 2230/0017; A61F 2230/0028; A61F 2230/0065; A61F 2230/0091; A61F 2250/0001; A61F 2250/0037; A61F 2250/0048; A61F 2250/0058; A61F 2310/00011; A61F 2310/00095; A61F 2310/00592; A61F 2310/0097; A61F 2310/00976; A61F 5/0059; A61F 5/0079; A61F 5/0116; A61F 5/024; A61F 5/05858; A61F 5/05875; A61F 5/3769; A61F 5/3776; A61F 5/3792; A61F 5/4401; A61F 6/22; A61F 6/225; A61F 7/12; A61F 7/123; A61F 9/00745; A61F 9/00772; A61F 9/02; A41B 11/02; A41B 11/003; A41B 11/14; A41B 2400/32; A41B 11/08; A41B 2400/38; A41B 11/12; A41B 11/121; A41B 11/005; A41B 11/126; A41B 2400/20; A41B 9/06; A41B 17/00; A41B 1/08; A41B 2400/60; A41B 2500/10; A41B 2400/34; A41B 3/00; A41B 11/123; A41B 2400/322; A41B 2500/30; A41B 9/001; A41B 1/00; A41B 11/001; A41B 11/006; A41B 2400/44; A41B 2300/332; A41B 11/008; A41B 11/06; A41B 11/143; A41B 2300/22; A41B 2400/22; A41B 2400/80; A41B 11/004; A41B 2300/326; A41B 2400/36; A41B 2500/50; A41B 2300/35; A41B 2500/20; A41B 11/007; A41B 11/146; A41B 3/02; A41B 9/00; A41B 11/002; A41B 11/01; A41B 11/04; A41B 2300/00; A41B 2400/00; A41B 9/02; A41B 9/12

USPC ....................................... 602/60–64; 606/201

See application file for complete search history.

(56) References Cited

U.S. PATENT DOCUMENTS

| | | | | | |
|---|---|---|---|---|---|
| 3,826,249 | A | * | 7/1974 | Lee ...................... | A61B 17/135<br>128/DIG. 20 |
| 3,871,301 | A | | 3/1975 | Dahl | |
| 2005/0113729 | A1 | * | 5/2005 | Scott ..................... | A61F 13/085<br>602/19 |
| 2006/0189913 | A1 | * | 8/2006 | Winkler .................. | A61F 13/08<br>602/61 |
| 2014/0163606 | A1 | * | 6/2014 | Ragg ................... | A61F 13/0253<br>606/201 |
| 2014/0309567 | A1 | * | 10/2014 | Wright ............... | A61B 17/1325<br>601/151 |
| 2016/0242946 | A1 | | 8/2016 | Gambardella et al. | |
| 2016/0310348 | A1 | * | 10/2016 | Farrow ................... | A61F 13/08 |
| 2018/0298530 | A1 | | 10/2018 | Gaither | |
| 2022/0132943 | A1 | * | 5/2022 | Bard ........................ | A41D 1/06<br>2/79 |

FOREIGN PATENT DOCUMENTS

| | | | | | |
|---|---|---|---|---|---|
| NZ | 710409 | | | 10/2017 | |
| WO | WO-2006134875 | A1 | * | 12/2006 | ............ A41B 11/00 |

* cited by examiner

COMPRESSION LEGWEAR WITH LINEAR PADS TO CONTROL SYMPTOMS OF VARICOSE VEINS

The present subject matter, directed in general to legwear, is more particularly directed to compression legwear including regions for controlling varicose vein symptoms.

BACKGROUND

Varicose veins are swollen, twisted, blood vessels that bulge just under the surface of a person's skin. They can be seen as blue or purple bulges, usually appearing in the legs, feet, and ankles. They can be painful or itchy. When veins in legs become enlarged, the valves in such veins do not function properly, causing bi-directional blood flow called "valvular reflux" in such veins. Moreover, as blood in such veins flows toward the feet, a condition called "venous hypertension" could develop, causing unpleasant symptoms including pain, swelling, skin discoloration, and in worst case scenarios, "venous ulcers."

Graduated compression hosiery has long been used in the medical industry, for example, to aid in prevention of deep vein thrombosis and help manage post-thrombotic syndrome. Further in this regard, graduated compression hosiery has known applications in managing varicose veins and, when used for everyday wear, help in terms of preventing tired, swollen, and generally uncomfortable legs, especially when traveling and pregnant.

One way of controlling the varicose veins of people thus afflicted is to manage the symptoms of venous valvular reflux in their legs by wearing medical grade 20-30 mm Hg firm compression stockings. However, many people find such medically recommended products difficult to put on—due to circumferential stresses—or uncomfortable to wear. With traditional compression stockings, an entire length of leg must be tightly compressed to decompress varicose veins, which explains why many people decide not to wear them.

The most common veins in the legs that are prone to developing valvular reflux are the great, small, and anterior saphenous veins. These three truncal veins are referred to as superficial veins because they are close to the surface of the skin. Unfortunately, due to their locations in the leg, the associated valves in the superficial veins often fail because they are not protected by the deep muscles and associated tissues, as are the deep veins. In addition, another risk factor for developing varicose veins is family history.

US published patent application 2018/0298530 to Gaither discloses a knit sock including a foot portion having an upper instep area and a lower sole area integrally knit of a body yarn in circumferential courses and axial wales. The lower sole area defines inner and outer arch regions. The inner arch region incorporates a targeted compression zone adapted to reside adjacent to an inner arch of a wearer's foot. The compression zone includes axially extending compression ridges of variable length spaced apart from an upper portion of the compression zone to a bottom portion of the zone. When the sock is worn, a compression force applied by the foot portion within a targeted compression zone is greater than the compression force in directly adjacent areas of said foot portion.

NZ 710409A in general, discloses anatomically targeted compression clothing and more particularly, discloses an item of clothing, adapted to be worn against the skin, and comprising at least one panel adapted to provide targeted compression of at least 20% of the total length of a surface vein selected from the cephalic vein or the basilic vein in the arm; the short saphenous vein or the long saphenous vein in the leg; the collection of drainage plexuses in the buttocks and lateral aspect of the hips, or the drainage plexus in the anterior chest wall overlying the pectoral muscles, or a combination thereof. The panel is located on the inside of the item of clothing and comprises a singular or plurality of protrusion(s) or pads, projecting inwardly towards the skin surface such that they act on the body, in use, to thereby provide a targeted compression. US published application 2014/0309567 to Wright et al. discloses a venous compression element said to be useful in treating chronic venous insufficiency, e.g., varicose veins. Such a compression element comprises a central core of fluid-filled cells and an outer layer of soft material said to be suitable for maintaining contact with skin for a prolonged period and for covering the central core. An embodiment comprises a folded or rolled cylindrical core of air or nitrogen-filled bubble-wrap material covered by a skin-compatible bandaging material. The compression elements described are also said to be useful in providing consistent compression to a blood vessel after endovenous endothelial wall damaging techniques.

My assessment of the latter two prior art references is as follows: They claim that compression elements/stockings can treat chronic venous insufficiency, or varicose veins. This is a false claim. There are no known compression stockings or sleeves that can treat chronic venous sufficiency or varicose veins. Compression stockings and sleeves are used as a conservative therapy. This means that they can only provide temporary relief to their wearers. Chronic venous insufficiency means that varicose veins disease had progressed and existed for a certain length of time. Also, as noted in this specification, the cause of chronic venous insufficiency in the lower extremity is valvular reflux in the saphenous veins. As of today, there is no technology or procedure available to fix or treat incompetent valves in veins yet. A defective or refluxing venous valve is an irreversible medical condition. While an endovenous laser treatment is a procedure available to treat abnormal saphenous veins, even laser ablation doesn't treat leaky valves. Rather, laser ablation treatment is a procedure that permanently closes abnormal saphenous veins.

Thus, the present subject matter does not claim to treat chronic venous insufficiency or varicose veins. Instead, one of the objects of this patent specification is to provide relief to people who are suffering from chronic venous insufficiency by controlling its symptoms and to disclose medical-grade compression socks, stockings, and/or sleeves adapted and configured to make it tolerable and acceptable for people who may otherwise refuse to wear them despite a recommendation by a physician. After an endovenous radiofrequency or laser-ablation treatment, patients are advised to wear compression stockings primarily to prevent the risk of thrombus from extending from a treated saphenous vein into the deep vein. Thrombus extension is a known complication of endovenous ablation procedures commonly referred to as endothermal heat-induced thrombosis ("EHIT"). The present subject matter—adapted and configured to deliver a medical-grade pressure along treated saphenous veins—can help prevent risk of EHIT while making it easier for patients to wear compression stockings during their recovery.

While saphenous veins are treated by damaging the endothelial wall using thermal heat, when the body senses that the superficial veins have already been obliterated and are no longer functioning, blood clot will form in the treated veins within 24 to 72 hours.

My linear pads, when applied along treated saphenous veins, ensure the diameter of varicose or dilated veins is reduced. By doing so, my pads minimize the formation of a blood clot. A newly formed blood clot-referred to as an acute blood clot—is soft in texture. Another important role of my pads is to ensure blood clots remain stable, so my pads, extending into select areas, do not move. Another object of the present subject matter is to prevent risk of EHIT and not simply aid in recovery and reduce inflammation.

SUMMARY

One embodiment of the present subject matter is directed to novel compression stockings designed to allow the stockings to be easier for a person to put on than other compression stockings and more comfortable to wear each day. They also apply surface pressure to select leg regions to decompress abnormal saphenous veins present there.

The medical-grade compression stockings of the present subject matter are made from fabric and elastic materials having a strength effective to provide a surface pressure of about 15-20 mm Hg circumferentially inwardly around the leg of a person having abnormal saphenous veins. Also, my compression stockings are manufactured with linear pads (of the same or similar materials) to apply constant pressure to the saphenous veins.

The medical-grade compression legwear of the present subject matter includes a thigh-high medical-grade compression stocking variety and a knee-high medical-grade compression sock variety. For the knee-high compression sock variety, two linear pads, each measuring about 4.0 cm wide and 6.0 mm thick extend from the knee to the ankle, medially and posteriorly. For the thigh-high compression stocking variety, in addition to the two linear pads noted above for the knee-high compression sock variety, compression stocking has another linear pad with a width of about 5.0 cm and a thickness of 8.0 mm extending from the proximal thigh to the knee medially, and another along the proximal thigh (about 10 cm in length) anteriorly. Specifications for the knee-high compression sock variety may also be used for various lower sections of thigh-high compression stockings.

This embodiment, directed to 15-20 mm Hg compression legwear designed to deliver a surface pressure of about 20-30 mm Hg to skin under which there are saphenous veins, does so with integrated linear pads. The pads, made of the same fabric and elastic material, are designed, sized, adapted, and configured to target locations of saphenous veins under the skin. For purposes of this patent specification, the term "pad" when used in connection with "a linear pad" shall be understood to mean a relatively thick piece of soft material that, by applying pressure to a surface, presses down upon a portion of that surface. After a pad is applied to a leg, the pad changes the surface contours of the skin. An applied pad increases pressure on the skin and decreases volume within surrounding soft tissue. As pads increase pressure above abnormal saphenous veins from 15-20 mm Hg to 20-30 mm Hg, varicose vein diameters reduce back to their normal size. Once this is accomplished, refluxing valves in the saphenous veins begin to work normally again.

Another embodiment of the present subject matter is directed to medical-grade compression sleeves to be worn on the legs of a person having abnormal saphenous veins. Compression sleeves of the present subject matter are easier for persons to put on their legs than other compression sleeves and are more comfortable to wear each day.

My medical-grade compression sleeves apply surface pressure to select leg regions to decompress abnormal saphenous veins present there. They are made from fabric and elastic materials having a strength effective to provide a surface pressure of about 15-20 mm Hg circumferentially inwardly around each leg of a person having abnormal saphenous veins. They are made to include linear pads of the same or similar materials, applying constant pressure to saphenous veins. Embodiments of the present subject matter may add an additional surface pressure of about 15-25 mm Hg or about 20-30 mm Hg or about 25-35 mm Hg to the skin under which there are saphenous veins.

While my compression sock and stocking embodiments may not be suitable for people with lymphedema and other non-vascular-related causes of swelling in feet, my compression sleeve embodiment is a better therapy solution for people who are suffering from chronic venous insufficiency for several reasons. Sleeves are easier to put on, more comfortable to wear, are less costly to manufacture, and linear pads are easier to attach.

The compression sleeves of the present subject matter include a thigh-high variety and a knee-high variety. For the knee-high variety, two linear pads, each measuring about 4.0 cm wide and 6.0 mm thick, extend from the knee to the ankle, medially and posteriorly. In addition, for the thigh-high variety, a linear pad having a width of about 5.0 cm and a thickness of 8.0 mm extends from the proximal thigh to the knee medially, and another pad extends along the proximal thigh (about 10 cm in length) anteriorly. Specifications for knee-high compression sleeve varieties may also be used for lower sections of thigh-high varieties. This compression sleeve embodiment, for 15-20 mm Hg sleeves designed and adapted to deliver a surface pressure of, e.g., about 20-30 mm Hg, to the skin under which there are saphenous veins, does so with integrated linear pads. Such pads, made of the same fabric and elastic material, are adapted and configured to target locations of saphenous veins under the skin of a leg of a person having abnormal saphenous veins.

BRIEF DESCRIPTION OF THE DRAWINGS

Throughout the figures—and the detailed description which follows—I shall use similar reference numerals, to refer to similar components of the present subject matter.

DETAILED DESCRIPTION

Compression socks and stockings (FIGS. 1-4) of the present subject matter are designed, dimensioned, and configured to use a technique called "targeted compression."

With targeted compression, an entire leg doesn't need to be tightly compressed. Instead, only those locations where the great, small, and anterior accessory saphenous veins are located, are firmly compressed by the linear pads of the present subject matter.

For purposes of the present subject matter, the term "pad" shall be understood to mean a relatively thick piece of relatively soft material adapted and configured to change the shape of something. Therefore, when a pad is applied to a leg, the pad changes the surface contour of the skin, increasing pressure in surrounding soft tissue and decreasing its volume. When applied thusly, a pad reduces the superficial vein diameter and when compression socks and stockings are worn, pressure at an arc length of a leg not covered by pads is 15-20 mm Hg, while pressure at an arc length of a leg covered by a pad of the present subject matter increases to about 20-30 mm Hg, as additional material pushes skin and soft tissue. A pressure of, e.g., about 20-30 mm Hg decompresses refluxing great, small, and anterior accessory saphenous veins, by reducing their size and enabling valves to work properly again. As a result, venous hypertension in lower legs is relieved.

The concept of targeted compression is based on a procedure involving ultrasound probe pressure. By using this procedure, varicose great, small, and anterior accessory saphenous veins decompress when adequate pressure is applied to the medial, posterior, and anterior sides of the legs using an ultrasound probe. The linear pads that are to be incorporated into designs of my compression socks and stockings function like ultrasound probes, to constantly apply pressure on locations where abnormal saphenous veins are.

Figure 1:
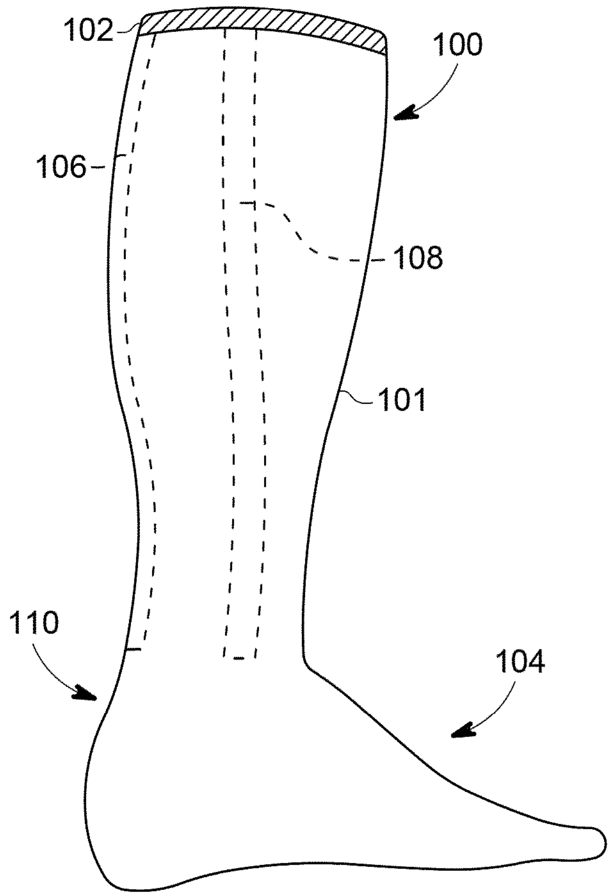
FIG. 1 depicts an embodiment of a knee-high compression sock of the present subject matter on a left leg, medial side, of a typical wearer of the compression stocking.
Figure 2:
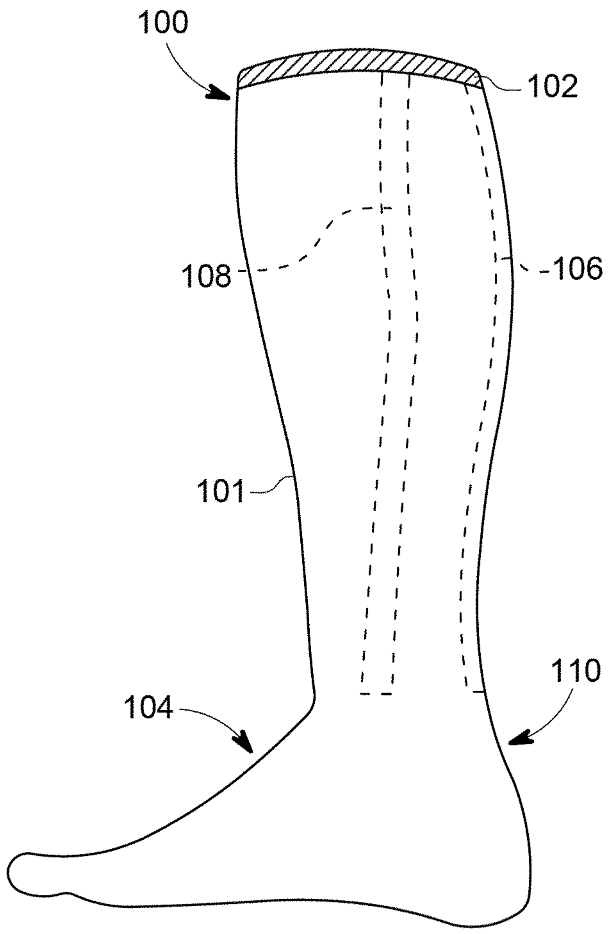
FIG. 2 depicts an embodiment of a knee-high compression sock of the present subject matter on a right leg, medial side, of a typical wearer of the compression stocking.

FIGS. 1-4 show embodiments of the present subject matter. FIGS. 1 and 2 depict embodiments of a knee-high compression sock of the present subject matter on a left leg (FIG. 1) and right leg (FIG. 2), medial side, of a typical compression sock wearer. FIGS. and 4 depict embodiments of a thigh-high compression stocking of the present subject matter on a left leg (FIG. 3) and right leg (FIG. 4), medial side, of a typical stocking wearer.

Referring to FIGS. 1 and 2, a knee-high compression sock 100 embodiment of the present subject matter has an upper margin 102, a lower region 104, and at least two linear pads 106 and 108 fixed to an inner surface of compression sock 100 and extending from upper margin 102 by a knee (not shown) to a lower region 104 below the ankle 110. Lower region 104 is sized, adapted, and configured to snuggly receive a foot of a person.

The linear pads 106 and 108 are elongated, vertically oriented, and spaced apart. Trailing edge-mounted linear pads 106 are vertically arranged along a wearer calf and are oriented about 90° from an associated medial-side pad 108. Each pad 106, 108 has a width ranging from about 1 cm to about 5 cm or from about 2 cm to about 5 cm or from about 3 cm to about 5 cm and has a thickness ranging from about 1 mm to about 8 mm or from about 2 mm to about 8 mm or from about 3 mm to about 8 mm or from about 4 mm to about 8 mm or from about 5 mm to about 8 mm or from about 6 mm to about 8 mm.

The sock 100 of the present subject matter includes a main body portion 101 made of spandex, a versatile fabric capable of being blended with other materials including but not limited to cotton, polyester, nylon, and combinations thereof for thereby providing a variety of fabrics and fabric blends for the present subject matter. For instance, a fabric blend ranging from about 23 weight-percent (wt.-%) spandex and 77 wt.-% nylon to about 27 wt.-% spandex and 73 wt.-% nylon is believed suitable for the present subject matter.

Figure 3:
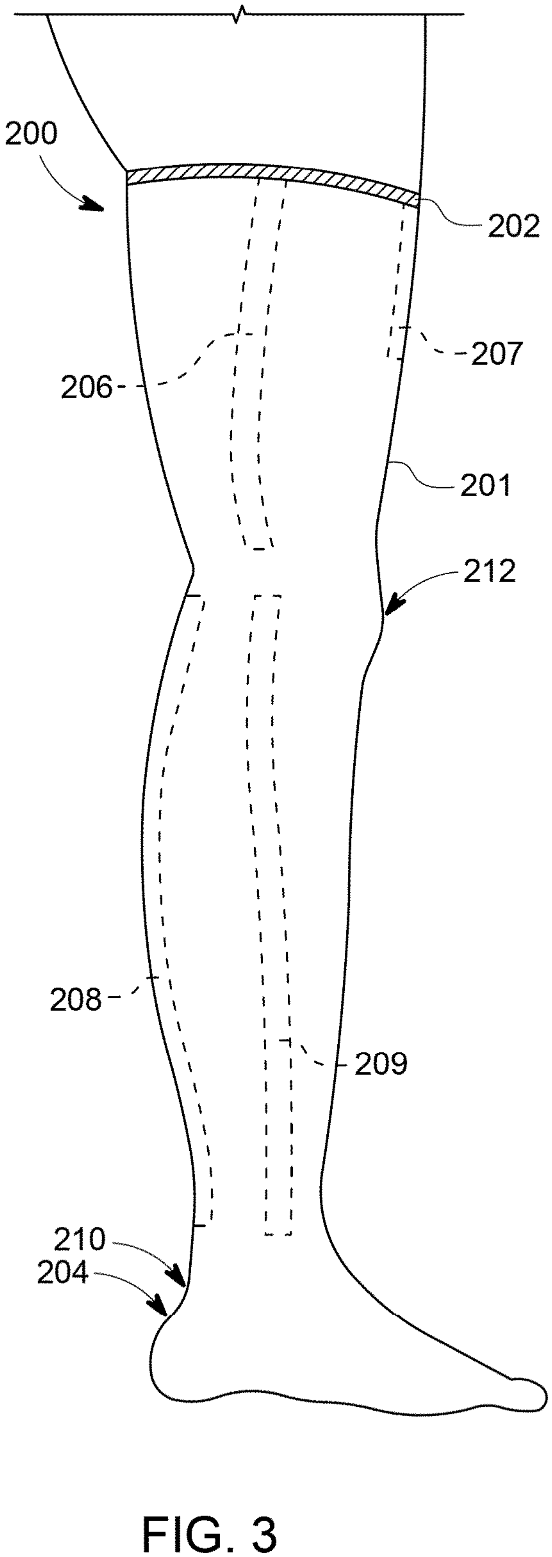
FIG. 3 depicts an embodiment of a thigh-high compression stocking of the present subject matter on a left leg, medial side, of a typical wearer of the compression stocking.
Figure 4:
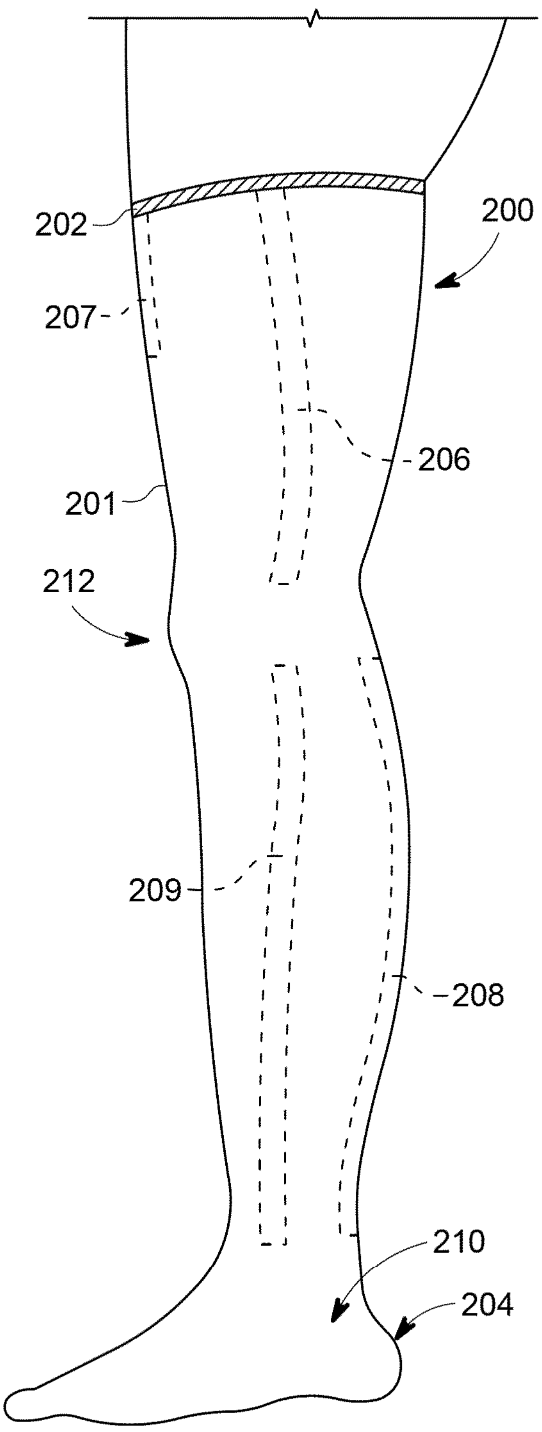
FIG. 4 depicts an embodiment of a thigh-high compression stocking of the present subject matter on a right leg, medial side, of a typical wearer of the compression stocking.

Referring next to FIGS. 3 and 4, an embodiment of a thigh-high compression stocking 200 of the present subject matter includes an upper margin 202, a lower region 204, and at least four linear pads 206-209 secured to an inner surface of the compression stocking 200 and extending either from the upper margin 202 to the lower region 204 or extending from the lower region 204 by ankle 210, and directed toward upper margin 202. Lower region 204 is sized, adapted, and configured to snuggly receive a foot of a person.

Each upper pad 206 and 207—is positioned along a thigh of a wearer of a stocking 200, with one upper pad 206 having a longer length than the other upper pad 207—has a width ranging from about 1 cm to about 5 cm or from about 2 cm to about 5 cm or from about 3 cm to about 5 cm and has a thickness ranging from about 1 mm to about 8 mm or from about 2 mm to about 8 mm or from about 3 mm to about 8 mm or from about 4 mm to about 8 mm or from about 5 mm to about 8 mm or from about 6 mm to about 8 mm.

Each lower pad 208 and 209—positioned along a calf of a wearer of a stocking 200, with lower pads 208, 209 each having substantially the same length and extending between an ankle 210 and a knee 212 of a wearer of stocking 200—has a width of ranging from about 1 cm to about 4 cm, or from about 2 cm to about 4 cm or from about 3 cm to about 4 cm, and has a thickness ranging from about 1 mm to about 6 mm, or from about 2 mm to about 6 mm, or from about 3 mm to about 6 mm, or from about 4 mm to about 6 mm.

The stocking 200 of the present subject matter includes a main body portion 201 made of spandex, a versatile fabric able to be blended with other materials including but not limited to cotton, polyester, nylon, and combinations thereof for thereby providing a variety of fabrics and fabric blends for the present subject matter. For instance, a fabric blend ranging from about 23 weight-percent (wt.-%) spandex and 77 wt.-% nylon to about 27 wt.-% spandex and 73 wt.-% nylon is believed suitable for the present subject matter.

Compression sleeves (FIGS. 5-8) of the present subject matter are also designed, sized, adapted, and configured to use the "targeted compression" technique noted above.

For purposes of the present subject matter, the term "pad" shall be understood to mean a relatively thick piece of relatively soft material sized, adapted, and configured to change the shape of a surface portion of a leg to which the pad is applied. When a pad is applied to a leg, the pad changes the surface contour of a portion of a leg to which the pad is applied, thereby increasing pressure within surrounding soft tissue and decreasing its volume. When applied thusly, a pad reduces the superficial vein diameter and when compression sleeves are worn, pressure at the arc length of a leg not covered by pads is 15-20 mm Hg, while pressure at the arc length of a leg covered by a pad of the present subject matter is increase to about 20-30 mm Hg, as the additional material pushes skin and soft tissue. A pressure of, e.g., about 20-30 mm Hg decompresses the refluxing great, small, and anterior accessory saphenous veins, by reducing their sizes and enabling their valves to work properly again. As a result, venous hypertension in lower legs is relieved.

The concept of targeted compression is based on a procedure involving ultrasound probe pressure. By using this procedure, the varicose great, small, and anterior accessory saphenous veins will decompress when adequate pressure is applied to the medial, posterior, and anterior sides of the legs using an ultrasound probe. The linear pads that are to be incorporated into designs of my compression sleeves function like ultrasound probes, to constantly apply pressure on locations where abnormal saphenous veins are.

Figure 5:
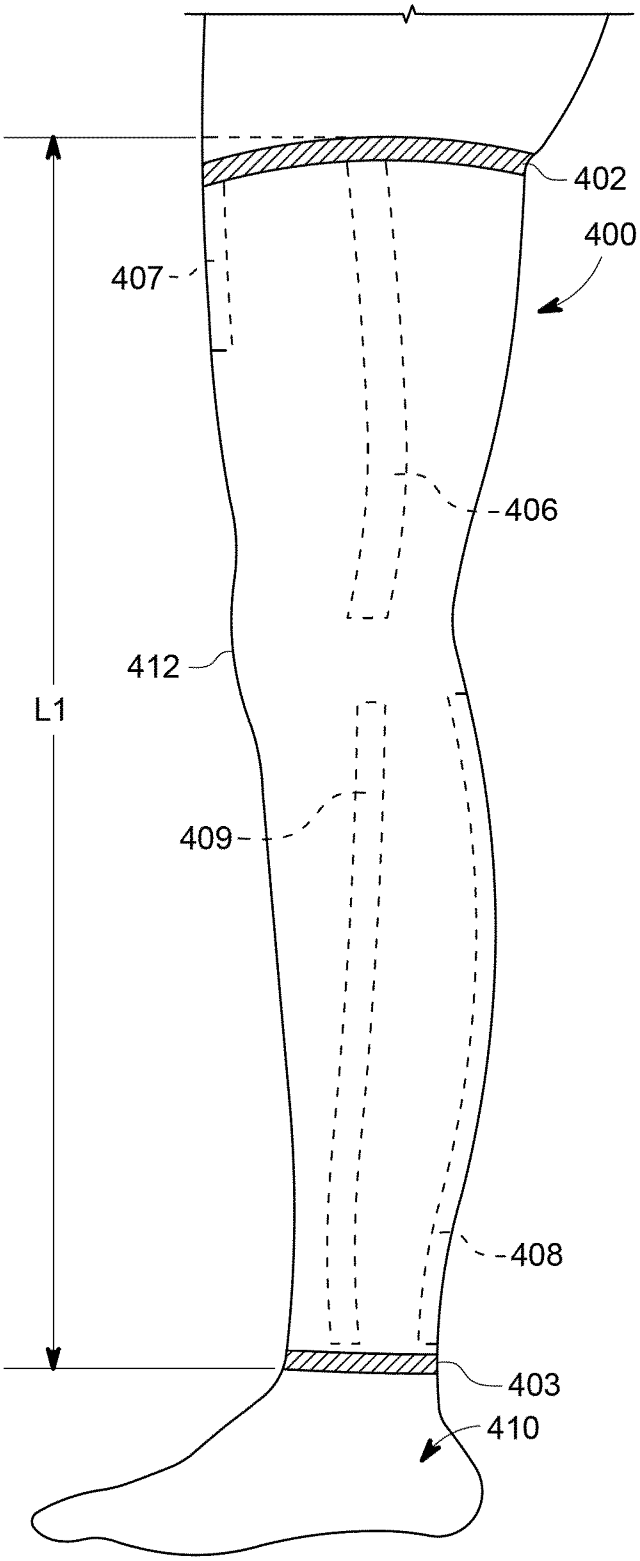
FIG. 5 depicts an embodiment of a thigh-high compression sleeve of the present subject matter on the right leg, medial side, of a typical wearer of the compression sleeve.
Figure 6:
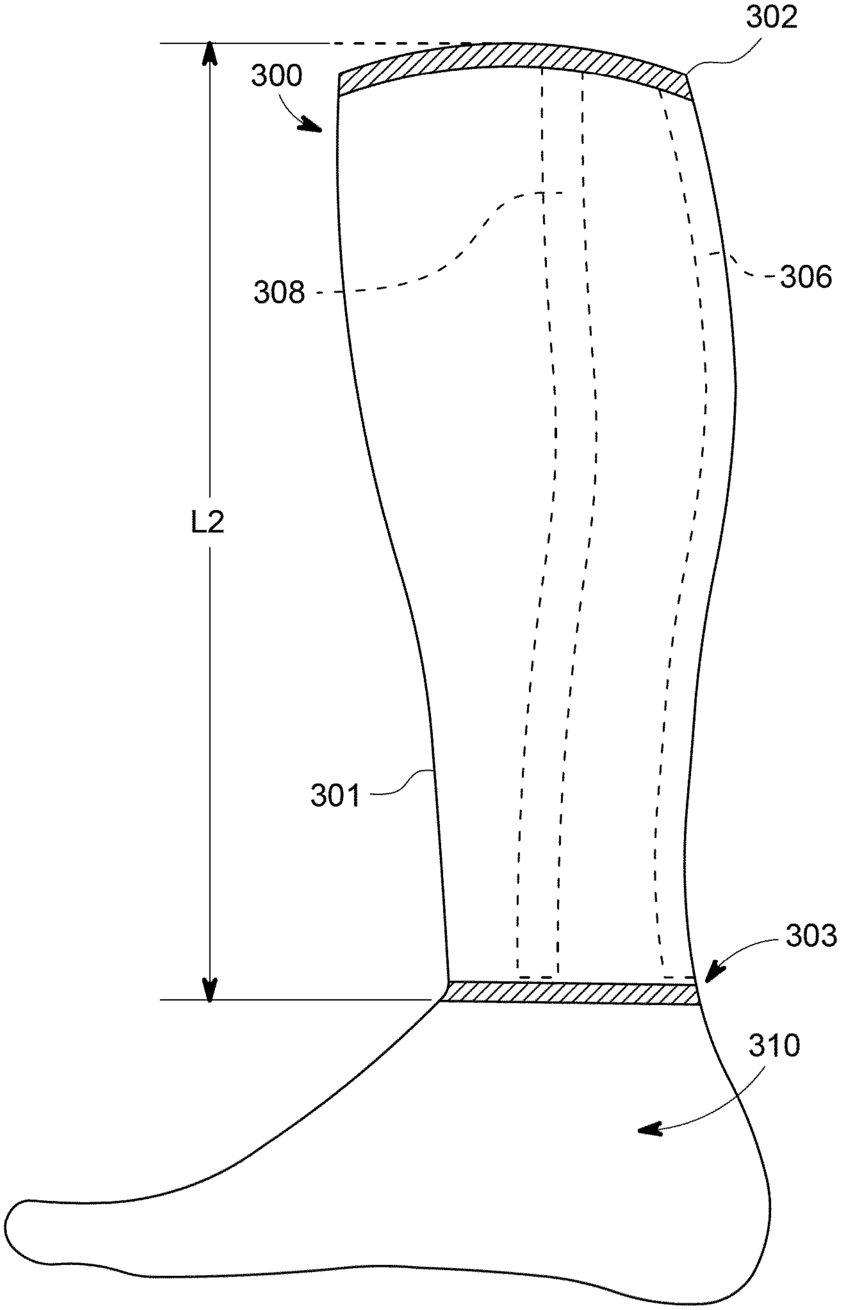
FIG. 6 depicts an embodiment of a knee-high compression sleeve of the present subject matter on the right leg, medial side, of a typical wearer of the compression sleeve.
Figure 7:
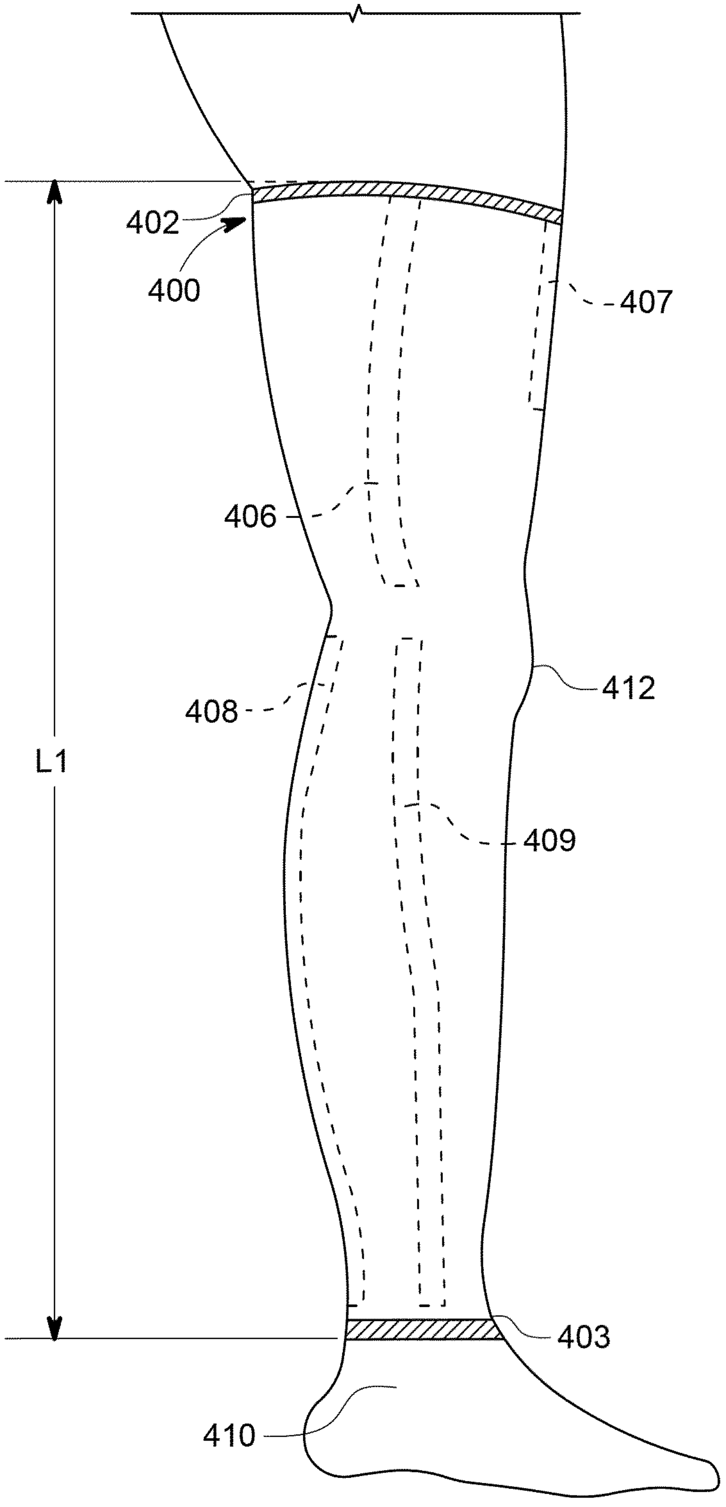
FIG. 7 depicts an embodiment of a thigh-high compression sleeve of the present subject matter on the left leg, medial side, of a typical wearer of the compression sleeve.
Figure 8:
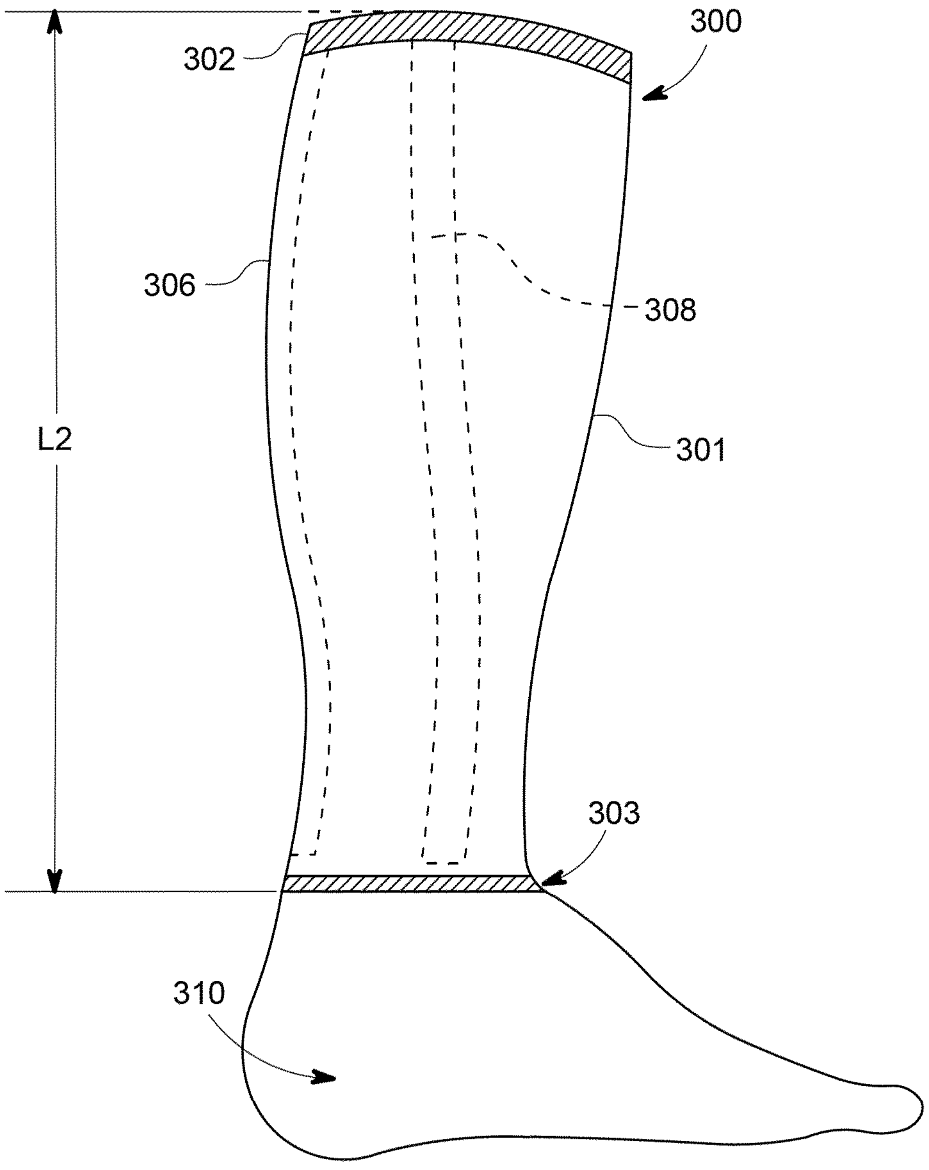
FIG. 8 depicts an embodiment of a knee-high compression sleeve of the present subject matter on the left leg, medial side, of a typical wearer of the compression sleeve.

FIGS. 5-8 also depict embodiments of the present subject matter. FIGS. 6 and 8 depict examples of a knee-high compression sleeve of the present subject matter on a left leg (FIG. 8) and right leg (FIG. 6), medial side, of a typical compression sleeve wearer. And FIGS. 5 and 7 depict examples of a thigh-high compression sleeve of the present subject matter on a left leg (FIG. 7) and right leg (FIG. 5), medial side, of a typical wearer.

Referring to FIGS. 6 and 8, an illustrative embodiment of a knee-high compression sleeve 300 of the present subject matter includes an upper margin 302, a lower margin 303, and at least two linear pads 306 and 308 secured to an inner surface of compression sleeve 300 and extending from the upper margin 302 to the lower margin 303 adjacent to an ankle 310 of a wearer of the knee-high compression sleeve 300. Depending upon the physical dimensions of a person, a knee-high compression sleeve 300 of the present subject matter may have a length ("L2") ranging from about 10 cm to about 80 cm or from about 15 cm to about 75 cm or from about 20 cm to about 70 cm or from about 25 cm to about 65 cm or from about 30 cm to about 60 cm or from about 35 cm to about 55 cm.

The linear pads 306 and 308 of the present subject matter are elongated. They are substantially vertically oriented when worn and are spaced apart. Trailing edge-mounted portions of elongated pads 306 are essentially vertically arranged along a wearer calf and are oriented about 90° from an associated medial-side pad 108. Each pad 306, 308 has a width ranging from about 1 cm to about 5 cm or from about 2 cm to about 5 cm or from about 3 cm to about 5 cm and has a thickness ranging from about 1 mm to about 8 mm or from about 2 mm to about 8 mm or from about 3 mm to about 8 mm or from about 4 mm to about 8 mm or from about 5 mm to about 8 mm or from about 6 mm to about 8 mm.

The sleeve 300 of the present subject matter includes a main body portion 301 made of spandex, a versatile fabric able to be blended with other materials including but not limited to cotton, polyester, nylon, and combinations thereof for thereby providing a variety of fabrics and fabric blends for the present subject matter. For instance, a fabric blend ranging from about 23 weight-percent (wt.-%) spandex and 77 wt.-% nylon to about 27 wt.-% spandex and 73 wt.-% nylon is believed suitable for the present subject matter.

Referring to FIG. 6, a circumferential distance between the vertically oriented linear pads 306 and 308 could vary within the range of between about 5 cm to about 30 cm or about 7 cm to about 25 cm or about 9 cm to about 20 cm or about 11 cm to about 15 cm.

Referring to FIGS. 5 and 7, an embodiment of a thigh-high compression sleeve of the present subject matter includes an upper margin 402, a lower margin 403, and at least four linear pads 406-409 secured to an inner surface of the compression sleeve 400 and extending either from the upper margin 402 to the lower margin 403. Thigh-high compression sleeve 400 has a length ("L1") ranging from about 10 cm to about 150 cm or from about 20 cm to about 140 cm or from about 30 cm to about 130 cm or from about 35 cm to about 125 cm or from about 40 cm to about 120 cm or from about 50 cm to about 115 cm from about 55 cm to about 110 cm or from about 60 cm to about 105 cm.

Each upper pad 406 and 407 of a thigh-high compression sleeve 400 is elongated, oriented vertically, and positioned on a thigh of a wearer, with medial side pads 406 each having a longer length than their associated forward-facing pads 407. Pads 406, 407 have a width ranging from about 1 cm to about 5 cm or from about 2 cm to about 5 cm or from about 3 cm to about 5 cm and has a thickness ranging from about 1 mm to about 8 mm or from about 2 mm to about 8 mm or from about 3 mm to about 8 mm or from about 4 mm to about 8 mm or from about 5 mm to about 8 mm or from about 6 mm to about 8 mm.

Each lower pad 408 and 409—positioned along a calf of a wearer of a sleeve 400, with lower pads 408 and 409 each having substantially the same length and extending between an ankle 410 and a knee 412 of a wearer of sock 400—has a width that ranges from about 1 cm to about 4 cm, or from about 2 cm to about 4 cm or from about 3 cm to about 4 cm, and has a thickness ranging from about 1 mm to about 6 mm, or from about 2 mm to about 6 mm, or from about 3 mm to about 6 mm, or from about 4 mm to about 6 mm.

The sleeve 400 of the present subject matter includes a main body portion 401 made of spandex, a versatile fabric able to be blended with other materials including but not limited to cotton, polyester, nylon, and combinations thereof for thereby providing a variety of fabrics and fabric blends for the present subject matter. For instance, a fabric blend ranging from about 23 weight-percent (wt.-%) spandex and 77 wt.-% nylon to about 27 wt.-% spandex and 73 wt.-% nylon is believed suitable for the present subject matter.

Referring to FIG. 5, a circumferential distance between vertically oriented linear pads 408 and 409 may vary within the range of between about 5 cm to about 30 cm or about 7 cm to about 25 cm or about 9 cm to about 20 cm or about 11 cm to about 15 cm. A circumferential distance between vertically oriented linear pads 406 and 407 may vary within a range of between about 10 cm to about 60 cm or about 15 cm to about 50 cm or about 18 cm to about 45 cm or about 22 cm to about 40 cm or about 25 cm to about 35 cm.

Embodiments of the present subject matter—including the knee-high compression sock 100, the thigh-high compression stocking 200, the knee-high compression sleeve 300, and the thigh-high compression sleeve 400 of the present subject matter—resolve the most common complaints of traditional compression stocking wearers: i.e., traditional compression stockings are said to be difficult to put on and too tight when worn. So how comfortable are the 15-20 mm Hg compression footwear with linear pads—of the present subject matter—in comparison to traditional 20-30 mm Hg compression socks/stockings? According to the Center for Disease Control ("CDC") and Prevention, the average calf circumference is 39.37 centimeters (15.5 inches) for male, and 38.1 cm (15.0 in) for female; overall mean calf circumference is 38.74 cm (15.25 in). Conventional knee-high padded compression stockings use a total width of about 8.0 cm for two pads. Pressure distribution in the calf with conventional knee-high compression stockings is as follows:

Unpadded parts of the stocking: 15-20 mm Hg around 28.74 cm of arc length.

Padded parts of the stocking: 20-30 mm Hg around 8.0 cm of arc length.

On a "personal comfort" (i.e., subjective) basis, it is believed a person of ordinary skill in the art ("POSITA") would conclude that knee-high 15-20 mm Hg compression stockings with linear pads—of the present subject matter—are about 79% more comfortable in the calves, compared to traditional 20-30 mm Hg compression stockings.

Based on body measurement data from the US Department of Health Statistics, the average circumference of men's thigh is 53.8 cm (21.2 inches), and for female is 52.9 cm (20.8 cm). The overall mean thigh circumference is 53.35 cm (21 inches). The pressure distribution in the thigh with thigh-high compression stockings is as follows:

Unpadded parts of the stocking: 15-20 mm Hg around 43.35 cm of arc length.

Padded parts of the stocking: 20-30 mm Hg around 10 cm of arc length.

Hence, it is believed a person of ordinary skill in the art ("POSITA") would conclude that the thigh-high 15-20 mm Hg padded compression stockings are about 81% more comfortable in upper legs, compared to traditional 20-30 mm Hg compression stockings.

There are at least two ways to attach elongated pads to my compression legwear. One way involves using commercially available elastic and/or flexible glues or adhesives. Illustrative examples include U.S. Pat. Nos. 3,515,773; 3,671,301; and U.S. Pat. No. 3,756,848 to Dahl; and U.S. Pat. No. 3,940,513 to Anderson-all of which are incorporated by reference in their entirety. Another way involves permanently securing elongated pads to my compression legwear by sewing and/or stitching a pad to a compression sock, stocking, or sleeve with a preselected material of predetermined strength such as nylon and/or polyester using, e.g., a zigzag stitch. I prefer to sew and/or stitch elongated pads to compression legwear.

Figure 9:
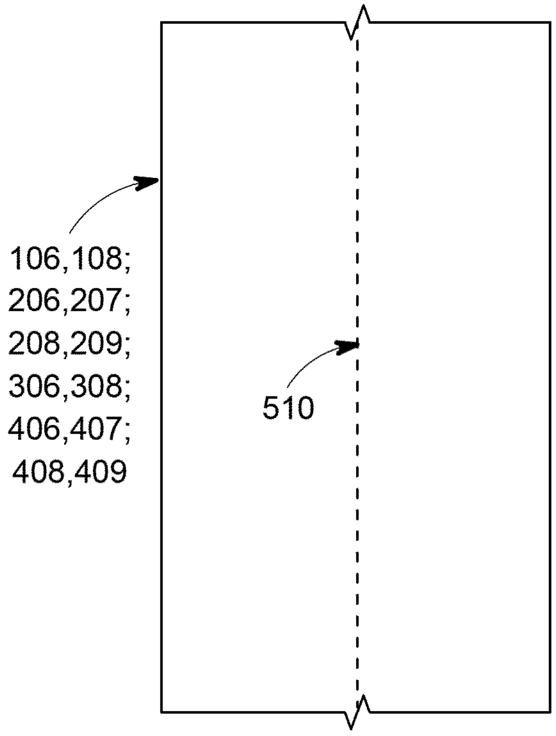
FIG. 9 presents an embodiment of a portion of a pad of the present subject matter.

FIG. 9 presents a portion of a pad of the present subject matter. Elongated pads 106, 108; 206, 207, 208, 209; 306, 308; 406, 407, 408, 409 may be produced with a partial or complete slit 510 along a length of a longitudinal pad from one end portion to the other. Pads may be secured to my compression legwear by sewing along slit 510 from one end portion to the other. After being secured, pad sections may be fused along the slit 510 using examples of commercially available elastic/flexible glues or adhesives listed above.

Described in detail in this patent specification are compression legwear including elongated linear pads to control symptoms of varicose veins. While the present subject matter is described with reference to present embodiments, the present subject matter is not limited to these embodiments. On the contrary, alternatives, changes, or modifications shall become apparent to a person of ordinary skill in the art ("POSITA") after this patent specification and its accompanying figures are reviewed. Therefore, all such alternatives, changes, and/or modifications are to be considered as constituting a part of the present subject matter insofar as they fall within the spirit and the scope of the appended claims.

The invention claimed is:

1. A compression stocking dimensioned, adapted, and configured to be worn by a wearer having varicose veins, wherein the stocking comprises:

a body having an upper margin and a lower region spaced from the upper margin, wherein the lower region is configured to be located closely adjacent to an ankle of the wearer, and wherein the lower region is sized, adapted and configured to snuggly receive a foot of the wearer;

and at least four elongated linear pads secured to an inner surface of the body, wherein a first two of the at least four pads are configured to extend from the lower region to an intermediate region configured to be located closely adjacent to a knee of the wearer of the stocking, wherein each of the first two of the at least four pads has a width ranging from 1 centimeter (cm) to 4 cm and a thickness ranging from 1 millimeter (mm) to 6 mm, wherein a second two of the at least four pads are configured to extend downwardly from the upper margin to the intermediate region configured to be located closely adjacent the knee, wherein each of the second two of the at least four pads has a width ranging from 1 cm to 5 cm and a thickness ranging from 1 mm to 8 mm, wherein each of the at least four pads is adapted and configured to exert a pressure of about 20-30 mm Hg to a varicose vein of the wearer of the stocking, wherein the at least four pads are spaced-apart and are oriented vertically, and wherein the at least four elongated pads are secured within the body and are configured to be located either closely adjacent to or overlaying the varicose veins of the wearer of the stocking.

2. The compression stocking of claim 1, wherein the at least four linear pads are adhesively secured to the inner surface of the body, wherein two of the at least four pads are configured to be located on a medial side of a leg of the wearer of the stocking, and wherein the other two of the at least four pads are configured to be located on an anterior side and on a posterior side of the leg of the wearer of the stocking.

3. The compression stocking of claim 1, wherein the at least four linear pads are sewn or stitched to the inner surface of the body, wherein two of the at least four pads are configured to be located on the body on a medial side of a leg of the wearer of the stocking, wherein another two of the at least four pads are configured to be located on an interior side and on a posterior side of the leg of the wearer of the stocking.

4. The compression stocking of claim 1, wherein the body is manufactured from spandex, and wherein the spandex is blended with a material selected from the group consisting of cotton, polyester, nylon, and combinations thereof.

5. The compression stocking of claim 1, wherein the body is made of from about 23 wt.-% spandex and about 77 wt.-% nylon to about 27 wt.-% spandex and about 73 wt.-% nylon.

6. A compression sock dimensioned, adapted, and configured to be worn by a wearer having varicose veins, wherein the sock comprises:

a body having an upper margin and a lower region spaced from the upper margin, wherein the lower region is configured to be located closely adjacent to an ankle of the wearer, and wherein the lower region is sized, adapted and configured to snuggly receive a foot of the wearer; and at least two elongated linear pads secured to an inner surface of the body, wherein each of the at least two elongated linear pads is configured to extend from the lower region to the upper margin configured to be located closely adjacent to a knee of the wearer of the sock, wherein each pad has a width ranging from 1 centimeter (cm) to 5 cm and a thickness ranging from 1 millimeter (mm) to 8 mm, wherein each of the at least two pads is adapted and configured to exert a pressure of about 20-30 mm Hg to a varicose vein of the wearer of the sock, wherein the at least two elongated linear pads are spaced-apart and are oriented vertically, and wherein said at least two elongated pads are secured within the body and configured to be located either closely adjacent to or overlaying the varicose veins of the wearer of the sock.

7. The compression sock of claim 6, wherein the at least two elongated linear pads are adhesively secured within the body to the inner surface of the body, wherein one of the at least two elongated linear pads is configured to be secured on a medial side of a leg of the wearer of the sock during use, and wherein the other one of the at least two elongated linear pads is secured to an anterior side or to a posterior side of the leg of the wearer of the sock.

8. The compression sock of claim 6, wherein the at least two elongated linear pads are sewn or stitched to the inner surface of the body, wherein one of the at least two elongated linear pads is located on the body on a medial side of a leg of the wearer of the sock during use, and wherein the other one of the at least two elongated linear pads is located on the body on an anterior side or on a posterior side of the leg of the wearer of the sock.

9. The compression sock of claim 6, wherein the body is manufactured from spandex, and wherein the spandex is blended with a material selected from the group consisting of cotton, polyester, nylon, and combinations thereof.

10. The compression sock of claim 6, wherein the body is made of from about 23 wt.-% spandex and about 77 wt.-% nylon to about 27 wt.-% spandex and about 73 wt.-% nylon.

* * * * *